Figure 1:
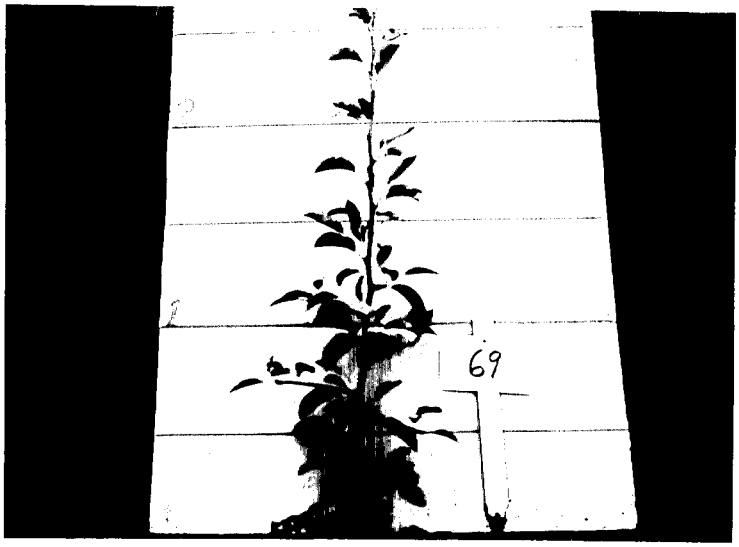
Figure 2:
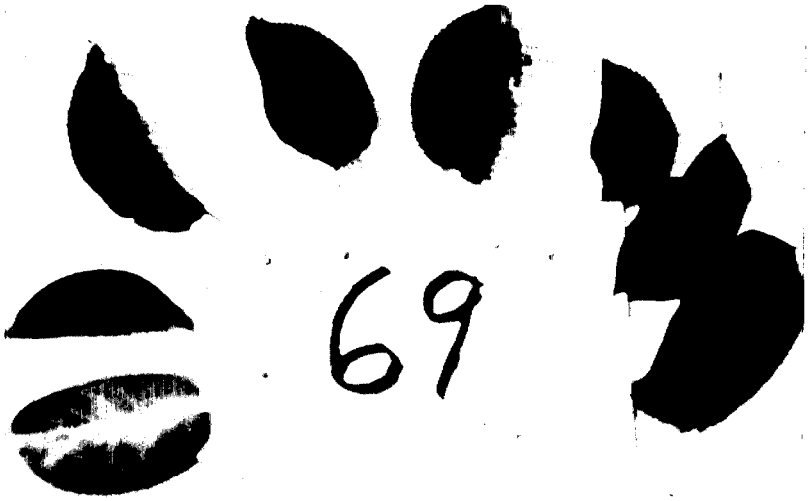
Figure 3:
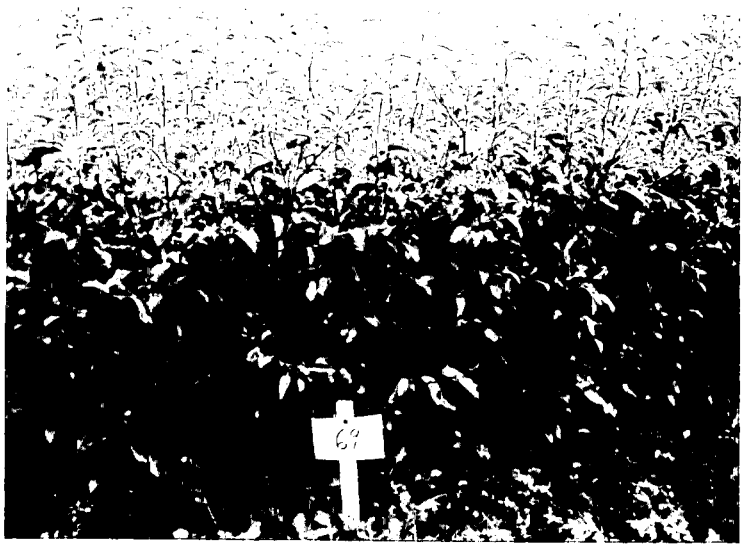
Figure 4:
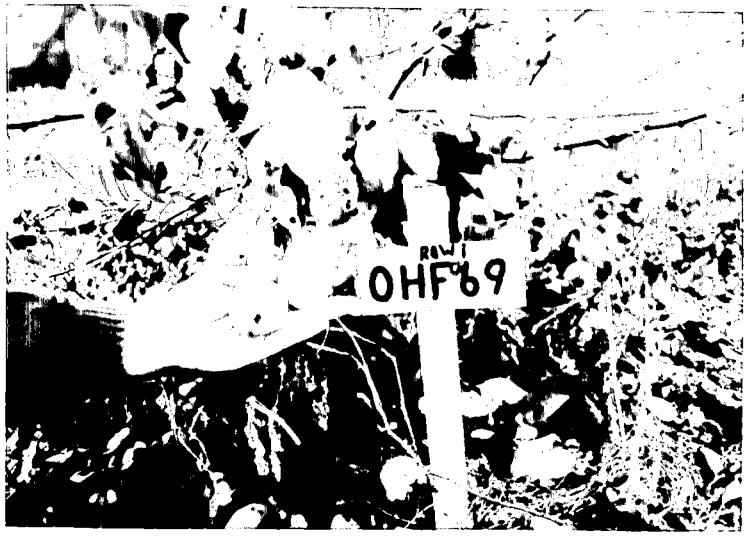
Figure 5:
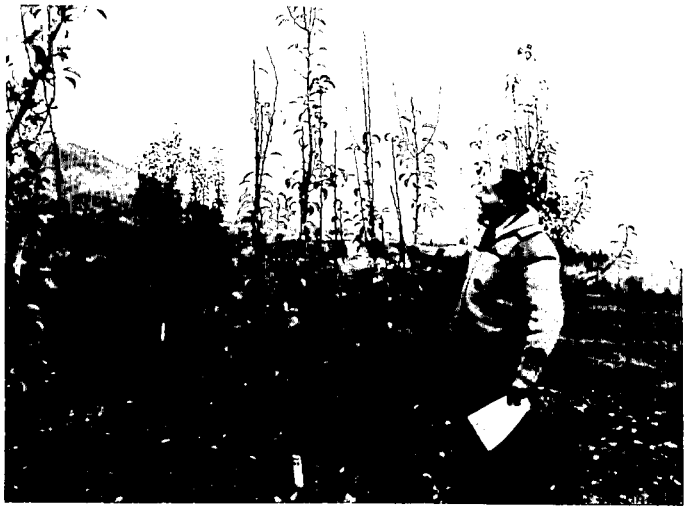
Figure 6:
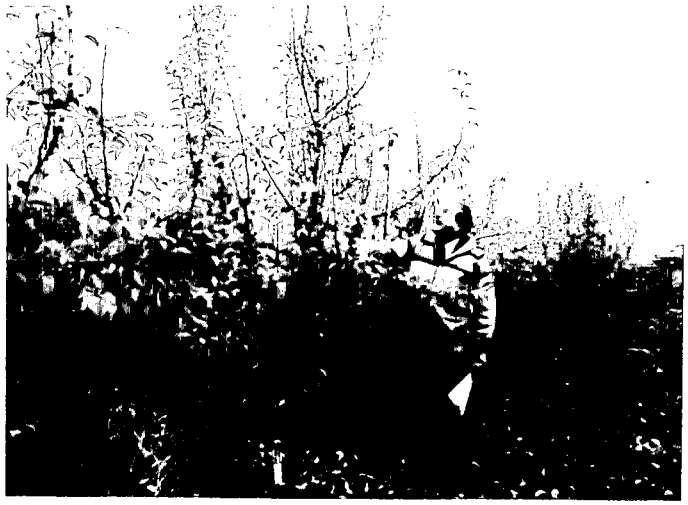
Figure 7:
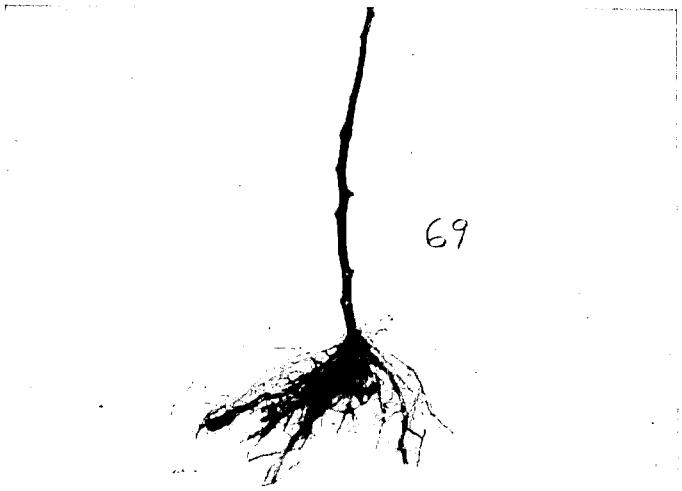

United States Patent [19]

Brooks

[11] Patent Number: Plant 5,559

[45] Date of Patent: Sep. 17, 1985

[54] PEAR TREE (VARIETY 69)

[75] Inventor: Lyle A. Brooks, Forest Grove, Oreg.

[73] Assignee: Carlton Nursery Company, Inc., Dayton, Oreg.

[21] Appl. No.: 534,179

[22] Filed: Sep. 20, 1983

[51] Int. Cl.[4] ..... A01H 5/03

[52] U.S. Cl. ..... Plt./36

[58] Field of Search ..... Plt./36

*Primary Examiner*—Robert E. Bagwill

*Attorney, Agent, or Firm*—Harvey B. Jacobson; Clarence A. O'Brien

[57] ABSTRACT

This invention relates to a new and distinct variety of pear tree (Variety 69) which is useful as a size-controlling pear rootstock. The new variety originated as a single seedling selected from a large group of pear seedlings which were grown from open-pollinated seed. This seed was harvested from Old Home pear trees (*Pryus communis*) growing in an isolated planting with Farmingdale pollinizers. Pear varieties grown on the understock of this new rootstock clone are approximately 75% of the size of like pear trees grown on Domestic Bartlett (*Pyrus communis*) seedling rootstocks. This "semi-dwarfing" selection can be easily increased by hard and softwood cuttings. It has proven to be graft-compatible with all major commercially grown pear varieties. It was selected for its non-root-suckering habit, its resistance to the Fireblight disease and its high tolerance of the Pear Decline disease. It has also proven to be hardy, early bearing, and well anchored in all areas and in all soil types where it was tested.

7 Drawing Figures

SUMMARY OF THE INVENTION

The original plant of this new variety was a member of a family of over 2000 pear seedlings which germinated from seed obtained from the Canadian Department of Agriculture Research Unit located near Summerland, British Columbia, Canada. This seed, collected from open-pollinated Old Home pear trees (*Pyrus communis*) which were growing in an isolated experimental planting with Farmingdale pollinizers, was planted by the inventor in his nursery at Forest Grove, Oreg. in 1952.

Experimental objectives were to develop, by trial and selection, a series of clonal pear rootstocks which would fulfill several urgent needs of both the orchardist and the nurseryman. The most important and immediate needs were for rootstocks that are resistant to Fireblight (*Erwinia amylovora*) a common, debilitating bacterial disease of pear trees. Also needed were rootstocks that are tolerant of the more recently described and equally destructive disease of pear known as Pear Decline. Pear Decline is a mycoplasma-caused disease which plugs pear phloem sieve tubes below the graft union causing decline and sometimes death of trees. This is particularly true if pear trees are propagated on non-tolerant seedling rootstocks. Most rootstocks used for pear tree propagation today are considered susceptible to this virus-like disease.

Another objective of this work was to select from the seedling population, rootstock clones which would root readily in the nursery by cuttings and/or by other vegetative means. The most major additional objective was to select from this seedling population a series of growth-controlling rootstock clones which could be made available to nurserymen and growers and which would permit them to develop orchards using tree spacing techniques tailored to known uniform tree sizes.

This objective can be accomplished only through the use of clonally propagated rootstocks.

All of these qualities are lacking in the seedling rootstocks currently being used in the trade today.

Old Home x Farmingdale #69 has shown its usefulness by exhibiting the following characteristics which fulfill all of the original desired objectives. It has been chosen as the best of several "semi-dwarfing" selections after nearly 30 years of orchard and nursery testing and evaluation.

Final selection was made in 1982 following tests which consisted of trial plantings and nursery evaluations which were carried out at Summerland, British Columbia; Clarksville, Ark.; Yakima, Wash.; Geneva, N.Y.; and Hood River, Salem, Medford, Corvallis, Dayton and Forest Grove, Oreg.

TEST AND EVALUATION RESULTS

1. Pear varieties grown on the rootstock of this variety are approximately 75% of the size of like pear trees grown on the most commonly used commercial pear rootstocks used in the trade. These are seedling rootstocks of Domestic Bartlett seed also known as Domestic pear seedlings (*Pyrus communis*). Trees grown on Bartlett seedling rootstocks are considered "standard" in size when established in the orchard and are used as the basis for all of the comparisons and measurements herein.

2. Due to its Old Home parentage, rootstocks of this clone have proven to be very Fireblight resistant in all areas where it was tested. In an arbitrary range of resistance, with Bartlett seedlings rated zero, this clone was rated as 90% resistant to the disease.

3. Pear trees grown on this rootstock have shown no Pear Decline symptoms in all tests and in all areas where trial plantings were observed.

It is believed to be Pear Decline tolerant with all major commercial varieties.

4. The new pear rootstock clone has been virus-indexed and found to be free of all known virus diseases of pear.

5. Trees on this clone have been rigidly inspected in the orchard for rootsuckering. Less than 1% of the trees observed on this rootstock, showed a tendency to rootsucker when tested over a 20 year period.

6. Yield efficiency, in tests run to date, has been about equal to trees on Bartlett seedling rootstocks. Yield efficiency was determined by comparing yield to unit of tree size.

7. Young Bartlett trees propagated on this rootstock variety have come into bearing at an early age. Heavy bloom and fruit set was noted and recorded during the third growing season in our numerous orchard trials. This compared to Bartlett trees on Domestic seedling rootstocks with light, sporatic fruit sets in their fourth growing season following planting in these plots.

8. The new rootstock selection has proven to be hardy in all areas where it was tested and is considered to be hardy wherever pears are grown.

9. This new and distinct rootstock is graft-compatible with all commercially grown pear varieties.

10. The new selection shows only average resistance to Pear Root-aphids.

11. Pear trees grown on this stock shown very good root-anchorage in all of the orchard sites and soil types where it was tested.

12. Pear rootstock trees of the Old Home x Farmingdale #69 variety can be easily propagated by hardwood and softwood cuttings and/or micropropagation methods (meristematic tissue culture). Such asexual reproductions have demonstrated that its distinctive characteristics and particularly including its "semi-dwarfing" character are stable and are transmitted without change through succeeding propagations and generations.

GENERAL AND DETAILED DESCRIPTION

Since Old Home x Farmingdale #69 is a variety intended to be used only as a rootstock for pear cultivars, the main detailed description and accompanying drawings will center on the vegetative parts rather than the flowers and fruits. This pear selection will be propagated only asexually rather than by seed, in order to maintain its clone characteristics. The accompanying pictures show typical specimens of this new clonal pear rootstock.

FIG. 1

This picture shows a one-year old shoot of Old Home x Farmingdale #69 taken from the cuttingbed showing its semi-spurry habit of growth, its straight upright stem and its slightly rolled leaves.

FIG. 2

This picture shows typical leaves of Old Home x Farmingdale #69 showing the finely-serrated margins. The long slender petiole is slightly channeled and is shown here with the long, narrow stipules at the base.

FIG. 3

This picture shows typical growth of Old Home x Farmingdale #69 in the nursery cuttingbed.

FIG. 4

This picture shows typical pyriform shaped fruit of Old Home x Farmingdale #69.

FIG. 5

This picture shows a seven year old Bartlett tree on a Old Home x Farmingdale #69 rootstock.

FIG. 6

This picture shows a seven year old Bartlett tree on the "standard" and commonly used Domestic Bartlett seedling rootstock.

FIG. 7

This picture shows a rooted hardwood cutting of Old Home x Farmingdale #69 taken from the cuttingbed showing typical root development at the basal cut.

DESCRIPTION OF VEGETATIVE CHARACTERISTICS

The following is a detailed description of the new pear rootstock's growth characteristics as observed on one year old shoots produced from hardwood cuttings which were grown in a cuttingbed located in the propagation nursey at Forest Grove, Oreg. These observations were made during the late growing season after vigorous summer growth had ceased but prior to fall leaf senescence. The new variety was also observed closely outdoors in the late fall during digging operations and again later in the tree storage warehouse where all stocks were evaluated for rooting characters prior to grading and storage. The characteristics described are those most often seen and used in the identification of a clonally propagated rootstock.

Colors of leaves and shoots herein described are based on their appearance at the site where stocks were grown, dug and stored. In those instances where a precise color assessment can be made, reference is to a Munsell Limit Color Cascade chart. In other instances, general color terms are used in accordance with their ordinary dictionary significance.

General habit:
- *Strength of growth.*—Vigorous, sturdy, stiff.
- *Habit.*—Upright, spurry.
- *Number of laterals (branching).*—Many, sturdy, stiff.

Wood-Summer:
- *Color.*—Greyish-green (21-12) on upper side, olive-green (23-12) on lower side.
- *Pubescence.*—None.
- *Texture.*—Smooth.

Wood-Winter:
- *Stoutness.*—Sturdy, stiff.
- *Diameter of shoots.*—5/16" Between buds, ⅜" across buds, 7/16" through buds.
- *Flexibility.*—Stiff.
- *Internodes.*—1½", Medium.
- Color.—Olive-green (23-12) on upper side, brownish-green (23-14) on lower side.
- *Pubescence.*—None.
- *Texture.*—Smooth.

Lenticels:
- *Number.*—Few.
- *Conspicuousness.*—Summer conspicuous.
- *Shape.*—Round, Raised.
- *Color.*—Whitish, turning to orange-brown (28-8).
- *Distribution.*—Scattered.
- *Size.*—Medium to large.

Leaves:
- *Size.*—Medium, length 2 7/16", breadth 1 5/8".
- *Shape.*—Elliptic.
- *Base.*—Obtuse, attenuated.
- *Apex.*—Mucronate, few twisted.
- *Serrations.*—Finely-serrate.

*Surface.*—Flat, shiny, few hairs along veins and midrib.

*Margin.*—Tending to turn up, slightly rolled.

*Pose in relation to stem.*—Erect.

*Color.*—Green (20-14) on upper surface, green (21-12) on lower surface.

*Pubescence.*—Few hairs mostly along midrib on upper surface, none on lower surface.

*Texture.*—Pliant, smooth upper surface, smooth lower surface.

*Color of tips of shoots.*—Pale yellowish-green (24-8) when still actively growing.

Petiole:

*Pubescence.*—None on upper surface, none on lower surface.

*Shape.*—Slender, slightly channeled.

*Length.*—Long, 1 1/6".

*Color.*—Green (22-11), pinkish on new growth.

*Pose.*—Erect, forming acute angle with stem.

*Glands.*—None.

Stipules (not always present):

*Size.*—Small.

*Margin.*—Smooth.

*Length.*—5/16".

*Color.*—Light-green (21-11).

*Pose.*—Mostly reposed along petiole.

Buds:

*Size.*—Small.

*Shape.*—Short, obtuse, pointed, conical.

*Color.*—Dark-brown, waxy.

*Pubescence.*—None.

*Pose.*—Somewhat appressed.

FLOWER AND FRUIT CHARACTERS

Flowers:

*Size.*—1¼" Across in dense clusters, showy.

*Color.*—White.

*Pedicels.*—⅜" Long, thick, pubescent, green.

Fruit (no commercial value but useful for identification):

*Size.*—2" Long, 1 ⅝" wide.

*Color.*—Yellow (26-6).

*Stem.*—1½", Thick, curved.

*Shape.*—Pyriform, roundish, obtuse.

GENERAL CHARACTERISTICS

Rootsuckering: Very rare.

Size control potential: "Semi-dwarf", about 75% of standard, less vigorous varieties more reduced in size.

Yield efficiency: About equal to that of trees worked on Domestic Bartlett seedling Rootstocks (*Pyrus communis*).

Compatibility: Graft-compatible with all major commercial fruiting varieties.

Rooting: Reproduces well by hardwood cuttings, roots arise mostly at basal cut.

Root anchorage: Excellent in all soil types tested.

Hardiness: Hardy wherever pears are grown.

Disease resistance: Highly resistant to Fireblight (*Erwinia amylovora*), tolerant of the Pear Decline mycoplasma organism, index tested and shown to be free of known pear viruses.

Pest resistance: Average resistance to common pests of pear.

Early bearing ability: Heavy bloom and fruit set during third growing season.

I claim:

1. A new and distinct variety of pear tree referred to by the cultivar designation Old Home x Farmingdale #69 and substantially as herein shown and described characterized particularly by its ability to serve as a rootstock for grafting of pear tree cultivars to produce "semi-dwarf" pear trees; further characterized by its resistance to the Fireblight disease and its tolerance of the Pear decline disease, further characterized by its non-rootsuckering habit, its hardiness, its excellent root-anchorage, its good compatibility with all major commercial pear varieties, its early bearing habit, and its ability to root easily and reproduce readily to hard and softwood cuttings.

* * * * *